(12) United States Patent
Nagasawa et al.

(10) Patent No.: US 6,541,614 B1
(45) Date of Patent: Apr. 1, 2003

(54) POLYSACCHARIDE DERIVATIVE

(75) Inventors: Atsushi Nagasawa, Wakayama (JP); Tomohito Kitsuki, Wakayama (JP); Takeshi Ihara, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/926,688

(22) PCT Filed: May 31, 2000

(86) PCT No.: PCT/JP00/03485
§ 371 (c)(1),
(2), (4) Date: Dec. 3, 2001

(87) PCT Pub. No.: WO00/73351
PCT Pub. Date: Dec. 7, 2000

(30) Foreign Application Priority Data

Jun. 1, 1999 (JP) .......................................... 11-153775

(51) Int. Cl.⁷ ......................... C07H 15/08; C08B 11/08; C08B 31/12; C08B 1/00; C08B 37/00

(52) U.S. Cl. ...................... 536/18.3; 536/4.1; 536/18.5; 536/17.2; 536/123.1; 536/124; 536/17.6; 536/97

(58) Field of Search ................................. 536/4.1, 1.11, 536/18.3, 18.5, 17.2, 123.1, 124, 17.6, 97

(56) References Cited

U.S. PATENT DOCUMENTS

| | | | |
|---|---|---|---|
| 3,760,881 A | * | 9/1973 | Kiel |
| 4,096,074 A | | 6/1978 | Stournas |
| 4,663,448 A | | 5/1987 | Chiu |
| 5,095,054 A | * | 3/1992 | Lay et al. |
| 5,273,772 A | * | 12/1993 | Cooper |

FOREIGN PATENT DOCUMENTS

| EP | 1 057 822 | 12/2000 |
|---|---|---|
| JP | 3-291295 | 12/1991 |

OTHER PUBLICATIONS

Ramin et al., Make–up removing Composition, U.S. patent application Publication, US 2002/0012643 A1; Jan. 3, 2002.*

* cited by examiner

Primary Examiner—Samuel Barts
Assistant Examiner—Michael C. Henry
(74) Attorney, Agent, or Firm—Oblon, Spivak, McClelland, Maier & Neustadt, P.C.

(57) ABSTRACT

Polysaccharide derivatives derived from a polysaccharide or a derivative thereof by substituting a part or all of the hydrogen atoms of the hydroxyl groups of the polysaccharide or the derivative thereof with the groups represented by the following formula (1):

$$—E^1—(OA)_n—E^2—R \qquad (1)$$

wherein $E^1$ represents a divalent saturated $C_{1-6}$ hydrocarbon group which may be substituted with one or more hydroxyl groups or oxo groups, n stands for a number of from 8 to 300, n numbers of As may be the same or different and each independently represent a divalent saturated $C_{1-6}$ hydrocarbon group, $E^2$ represents an ether bond or an oxycarbonyl group, and R represents a $C_{4-30}$ alkyl group which may be substituted with one or more hydroxyl groups, in which the H(s) of one or more hydroxy groups in each of said groups (1) may be further substituted with the groups (1); thickeners and emulsifiers comprising these polysaccharide derivatives; as well as aqueous compositions containing said polysaccharide derivatives.

The polysaccharide derivatives of the present invention are excellent in water solubility and have such a rheological characteristic that the viscosity thereof increases at high temperatures, whereby they are very useful as a thickener exhibiting an excellent handling property at low temperatures and a sufficient thickening effect at high temperatures, as an emulsifier exhibiting an excellent emulsifying action allowing hydrophobic compounds to exist very stably in water, and also as a thickening and stabilizing agent for various toiletry products such as viscous bath preparations, massaging cosmetic preparations, shower preparations, skin care preparations, hair washing preparations, body washing preparations, garment detergents, garment finishing agents and hard surface cleaning agents.

30 Claims, No Drawings

POLYSACCHARIDE DERIVATIVE

This is the National Phase Application of PCT/JP00/03485, filed May 31, 2000.

1. Technical Field

This invention relates to novel polysaccharide derivatives, specifically novel polysaccharide derivatives having such unique thickening action that the viscosity thereof increases at a higher temperature than at room temperature and also having a high stabilizing action for hydrophobic substances contained in water, a process for their production, and an aqueous composition containing the polysaccharide derivative.

2. Background Art

Cellulose ethers such as methylcellulose and hydroxyethylcellulose or polyacrylic acid compounds such as "Carbopol" are widely used as a thickener, i.e. one of the important ingredients of cosmetic preparations, toiletry products and the like.

These thickeners, however, have such a rheological characteristic that the viscosity thereof decreases at a high temperature. These thickeners hence are accompanied with such problems that no sufficient viscosity is obtainable when applied for showering agents, bath preparations or the like used in a high-temperature environment such as bathroom, or when the thickeners are used in a larger amount in these products to provide a certain viscosity, the viscosity of the product increases during storage at room temperature, which makes dispensing the products from containers difficult or handling the products inconvenient.

An object of the present invention is, therefore, to provide a thickener having such a Theological characteristic that the viscosity increases at a high temperature, for example, when used in warm water or on the skin, but decreases at room temperature.

3. Disclosure of the Invention

The present inventors have found that novel polysaccharide derivatives, in which the hydrogen atoms of the hydroxyl groups of polysaccharides are substituted with specific polyoxyalkylene-containing groups, have such unique Theological characteristic as described above, an excellent water solubility and improved handling property at low temperatures, and provide a sufficient thickening property at high temperatures, for example, when used in warm water or on the skin, and thus are extremely useful as a thickener and a stabilizer for various toiletry products such as bath preparations, massaging cosmetic preparations, shower preparations, skin care preparations, hair washing preparations, body washing preparations, garment detergents, garment finishing agents and hard surface cleaning agents.

Specifically, the present invention provides a polysaccharide derivative derived from a polysaccharide or a derivative thereof by substituting a part or all of the hydrogen atoms of the hydroxyl groups of the polysaccharide or the derivative thereof with the following substituent groups (A):

(A) groups represented by the following formula:

$$—E^1—(OA)_n—E^2—R \quad (1)$$

wherein $E^1$ represents a linear or branched, divalent, saturated $C_{1-6}$ hydrocarbon group which may be substituted with one or more hydroxyl groups or oxo groups, n represents a number of from 8 to 300, n numbers of As may be the same or different and each independently represents a linear or branched, divalent, saturated $C_{1-6}$ hydrocarbon group, $E^2$ represents an ether bond or an oxycarbonyl group (—OCO— or —COO—), and R represents a linear or branched $C_{4-30}$ alkyl group which may be substituted with one or more hydroxyl groups, wherein the hydrogen atom(s) in one or more hydroxy groups in each of the substituent groups (A) may be further substituted with the substituent groups (A) as defined above, as wells a process for their production.

Further, the present invention provides a thickener and an emulsifier, each of which comprises the above-described polysaccharide derivative.

Furthermore, the present invention also provides an aqueous composition comprising the above-described polysaccharide derivative.

Best Modes for Carrying Out the Invention

For example, when a cellulose is used as the polysaccharide or the derivative thereof, the recurring unit of the polysaccharide derivative according to the invention can be represented by the following formula:

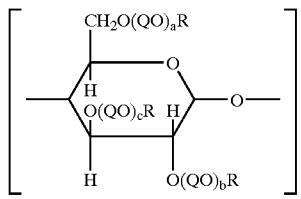

wherein R may be the same or different and each independently represents a group selected from (1) hydrogen, methyl, ethyl, hydroxyethyl or hydroxypropyl or the like, (2) a polyoxyalkylene-containing substituent group (A), (3) a sulfoalkyl group (B), (4) a carboxyalkyl group (C), and (5) a cationic substituent group (D); Q may be the same or different and each independently represents a $C_{2-4}$ alkylene group; a, b and c may be the same or different and each independently represent a number of from 0 to 10; and wherein the groups QO and R, as well as a, b and c in the same recurring unit or in the different recurring units may be the same or different; and wherein one or more hydroxyl groups in each of the substituent groups (A)–(D) may be further substituted with the other substituent groups (A)–(D), with the proviso that at least one of the Rs is substituent group (A).

As $E^1$ in the formula (1) representing the polyoxyalkylene-containing substituent (A), those having 2 or 3 carbon atoms are preferred. Specifically, ethylene, propylene, trimethylene, 2-hydroxytrimethylene, 1-hydroxymethylethylene, 1-oxoethylene, 1-oxotrimethylene and 1-methyl-2-oxoethylene are preferred.

As A in the formula (1), those having 2 to 3 carbon atoms are preferred. Specifically, ethylene, propylene and trimethylene are preferred. The polymerization degree of (—OA—) as indicated by n is preferably 8 to 120, particularly 10 to 60, in view of thickening effect and emulsion stabilizing action. The "n" number of "A"s may be the same or different. The letter "n" as used herein means an average molar number of (OA). While $E^2$ represents an ether bond or an oxycarbonyl group, an oxycarbonyl group is preferred.

As R in the formula (1), linear or branched alkyl groups having 5 to 25 carbon atoms, especially 6 to 20 carbon atoms are preferred. From the viewpoint of stability, alkyl groups, especially linear alkyl groups are preferred. Specifically, octyl, decyl, dodecyl, tetradecyl, hexadecyl, octadecyl, isostearyl and the like are preferred.

The degree of substitution with the substituent groups (A) in the polysaccharide derivative according to the present invention is preferably in a range of from 0.0001 to 1.0, more preferably in a range of from 0.0005 to 0.5, particularly preferably in a range of from 0.001 to 0.1 per constituent monosaccharide residual group.

In addition to the substituent groups (A), the polysaccharide derivative according to the present invention may be further substituted with one or more groups selected from the substituent groups (B), (C) and (D) described below. In addition, the hydrogen atom(s) in one or more hydroxyl group(s) contained in each of the substituent groups (A) to (D) may be further substituted with the substituent groups (A) to (D).

(B) $C_{1-5}$ sulfoalkyl groups or salts thereof, each of which may be substituted with one or more hydroxyl groups:

Illustrative examples of the substituent groups (B) are 2-sulfoethyl, 3-sulfopropyl, 3-sulfo-2-hydroxypropyl, and 2-sulfo-1-(hydroxymethyl)ethyl. Among these, 3-sulfo-2-hydroxypropyl is preferred from the viewpoint of stability and production. All or some of these substituent groups (B) may be in the form of salts with Group 1 or Group 2 elements such as Na, K, Ca or Mg or an organic cation such as amine or ammonium ion. The degree of substitution with these substituents (B) is preferably in a range of from 0 to 1.0, more preferably in a range of from 0 to 0.8, particularly preferably in a range of from 0 to 0.5 per constituent monosaccharide residual group.

(C) $C_{2-6}$ carboxyalkyl groups or salts thereof, each of which may be substituted with one or more hydroxyl groups:

Illustrative examples of the substituent groups (C) are carboxymethyl, carboxyethyl, carboxypropyl, carboxybutyl and carboxypentyl. Among these, carboxymethyl is preferred from the viewpoint of stability and production. All or some of these substituent groups (C) may be in the form of salts with Group 1 or Group 2 elements such as Na, K, Ca or Mg, or organic cations such as amine or ammonium ion. The degree of substitution with these substituents (C) is preferably in a range of from 0 to 1.0, more preferably in a range of from 0 to 0.8, particularly preferably in a range of from 0 to 0.5 per constituent monosaccharide residual group.

(D) The groups represented by the following formula (2):

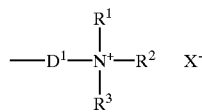
(2)

wherein $D^1$ represents a linear or branched, divalent, saturated $C_{1-6}$ hydrocarbon group which may be substituted with one or more hydroxyl groups; $R^1$, $R^2$ and $R^3$ may be the same or different and each independently represent a linear or branched $C_{1-3}$ alkyl group which may be substituted with one or more hydroxyl groups; and $X^-$ represents a hydroxy ion, a halogen ion or an organic acid ion.

As $D^1$ in the cationic substituent group (D), those having 2 or 3 carbon atoms are preferred. Specifically, ethylene, propylene, trimethylene, 2-hydroxytrimethylene, 1-hydroxymethylethylene and the like are preferred.

Examples of $R^1$, $R^2$ and $R^3$ in the cationic substituent group (D) include methyl, ethyl, propyl and 2-hydroxyethyl, with methyl and ethyl being preferred.

Examples of the halogen ion for $X^-$ in the cationic substituent group (D) include chlorine ion, bromine ion and iodine ion. Examples of the organic acid ion include $CH_3COO^-$, $CH_3CH_2COO^-$ and $CH_3(CH_2)_2COO^-$. Preferred examples of $X^-$ include hydroxy ion, chlorine ion and bromine ion.

The degree of substitution with these cationic substituent groups (D) is preferably in a range of from 0 to 0.5, particularly in a range of from 0 to 0.3 per constituent monosaccharide residual group.

The polysaccharide derivative according to the present invention can be produced, for example, by reacting a polysaccharide or a derivative thereof with a polyoxyalkylating agent (a) represented by the following formula (3):

(3)

wherein $E^3$ represents an epoxylated $C_{3-6}$ alkyl group, a halogenated linear or branched $C_{1-6}$ alkyl group which may be substituted with one or more hydroxyl groups, or a carboxyl or $C_{2-6}$ carboxyalkyl group or a derivative thereof, and n, A, $E^2$ and R have the same meanings as defined above, and optionally further reacting the resulting polysaccharide derivative with one or more compounds selected from the following compounds (b), (c) and (d):

(b) a sulfonating agent selected from a vinylsulfonic acid, a $C_{1-5}$ haloalkanesulfonic acid which may be substituted with one or more hydroxyl groups, an epoxy-containing $C_{2-6}$ sulfonic acid and salts thereof, (c) a carboxylating agent selected from a halogenated $C_{2-6}$ carboxylic acid which may be substituted with one or more hydroxyl groups and salts thereof, and (d) a cationizing agent represented by the following formula (4):

(4)

wherein $D^2$ represents an epoxylated $C_{3-6}$ alkyl group, or a halogenated, linear or branched $C_{1-6}$ hydrocarbon atom which may be substituted with one or more hydroxyl groups, and $R^1$, $R^2$, $R^3$ and $X^-$ have the same meanings as defined above.

Namely, the polysaccharide derivative according to the present invention can be obtained by polyoxyalkylating all the hydrogen atoms in the hydroxyl groups contained in a polysaccharide or its derivative [introduction of substituent groups (A)], or by partly polyoxyalkylating said hydrogen atoms [introduction of substituent groups (A)] and, as necessary, conducting sulfonaton [introduction of sulfoalkyl groups (B)], carboxylation [introduction of carboxyalkyl groups (C)] and/or cationization [introduction of cationic substituent groups (D)]. These polyoxyalkylation reaction, sulfonation reaction, carboxylation reaction and/or cationization reaction can be carried out in any order, or two to four of these reactions can be conducted at the same time. It is, however, preferred to conduct the reactions in the order of polyoxyalkylation reaction, cationization reaction, carboxylation reaction and/or sulfonation reaction.

Examples of the polysaccharide or its derivative usable as a starting material in the present invention include polysaccharides such as cellulose, guar gum, starch, pullulan, dextran, fructan, mannan, agar, carrageenan, chitin, chitosan, pectin, alginic acid, and hyaluronic acid; and their derivatives substituted with methyl, ethyl, hydroxyethyl and/or hydroxypropyl groups, or the like. One or a combination of two or more substituent groups can be introduced into constituent monosaccharide residual groups. Illustrative of the resulting polysaccharide derivative include hydroxyethylcellulose, hydroxyethyl ethylcellulose, hydroxyethyl guar, hydroxyethyl starch, methylcellulose, methylguar, methylstarch, ethylcellulose, ethylguar gum, ethylstarch, hydroxypropylcellulose, hydroxypropyl guar gum, hydroxypropyl starch, hydroxyethyl methylcellulose, hydroxyethylmethylguar gum, hydroxyethylmethylstarch, hydroxypropylmethylcellulose, hydroxypropylmethylguar gum, and hydroxypropyl methylstarch. Among these starting polysaccharides or the derivatives thereof, cellulose, starch, hydroxyethylcellulose, methylcellulose, ethylcellulose and hydroxypropylcellulose are preferred, with hydroxyethylcellulose being particularly preferred. Substituent groups in the above-described polysaccharide derivatives can achieve a degree of substitution higher than 3.0 per constituent monosaccharide residual group by further substituting the hydroxyl groups of hydroxyethyl or hydroxypropyl groups to form, for example, polyoxyethylene chains or the like. The degree of substitution per constituent monosaccharide residual group of the polysaccharide derivative is preferably 0.1 to 10.0, particularly preferably 0.5 to 5.0. The weight average molecular weight of the starting polysaccharide or its derivative is preferably in a range of from 10,000 to 10,000,000, more preferably from 100,000 to 5,000,000, particularly preferably from 300,000 to 2,000,000.

The polyoxyalkylation reaction, sulfonation reaction, carboxylation reaction and cationization reaction will be hereinafter described.

(Polyoxyalkylation Reaction)

The polyoxyalkylation reaction of a polysaccharide or a derivative thereof is conducted by dissolving or dispersing the polysaccharide or derivative in a suitable solvent and reacting it with the polyoxyalkylating agent (a) represented by the formula (3).

Among the groups represented by $E^3$ in the formula (3), the epoxylated $C_{3-6}$ alkyl group includes 3-epoxypropyl, 3,4-epoxybutyl, 4,5-epoxypentyl and 5,6-epoxyhexyl groups. The halogenated linear or branched $C_{1-6}$ alkyl group which may be substituted with one or more hydroxyl groups includes 2-chloroethyl, 3-chlorpropyl, 4-chlorobutyl, 6-chlorohexyl, 2-bromoethyl, 2-hydroxy-3-chloropropyl and 1-hydroxymethyl-2-chloroethyl groups. The $C_{2-6}$ carboxyalkyl group includes carboxymethyl, carboxyethyl, carboxypropyl, carboxydibutyl, and carboxypentyl groups. Illustrative of these carboxyalkyl or carboxy derivatives include methyl esters, ethyl esters, acid halides, tosylated products, mesylated products, and anhydrides. Preferred examples of $E^3$ include 2,3-epoxypropyl; 2-chloroethyl, 3-chloropropyl, 2-hydroxy-3-chloropropyl; carboxymethyl, carboxyethyl, and their methyl esters and their acid halides.

The polyoxyalkylating agent (3) can be used either singly or in combination of two or more. The amount of the polyoxyalkylating agent can be optionally adjusted depending upon the desired amount of substituent groups (A) to be introduced into the polysaccharide or its derivative. In general, however, it is preferred to use the polyoxyalkylating agent in an amount of from 0.0001 to 10 equivalents, especially from 0.00015 to 5 equivalents per constituent monosaccharide residual group of the polysaccharide or its derivative.

This reaction is preferably conducted in the presence of an alkali or in the presence of an acid, as necessary. Examples of the alkali include hydroxides, carbonates and bicarbonates of Group 1 or Group 2 elements and tertiary amines, with sodium hydroxide, potassium hydroxide, calcium hydroxide, magnesium hydroxide and pyridine being preferred. Use of the alkali in an amount of from 1.0 to 10 molar times, especially from 1.05 to 5.0 molar times of the used polyoxyalkylating agent (3) provides good results and is preferred. Examples of the acid include mineral acids and organic acids, with sulfuric acid, hydrochloric acid, p-toluenesulfonic acid and methanesulfonic acid being preferred. Use of the acid in an amount of from 0.01 to 0.5 molar times, especially from 0.1 to 0.3 molar times of the used polyoxyalkylating agent provides good results and is preferred.

Examples of the solvent include lower alcohols, for example, isopropyl alcohol and tert-butyl alcohol. In order to enhance the reactivity between the polysaccharide or its derivative and the polyoxyalkylating agent (3), it is also possible to use a mixed solvent obtained by adding 0.1 to 100 wt. %, more preferably 1 to 50 wt. % of water to a lower alcohol.

The reaction temperature is preferably in a range of from 0 to 150° C., particularly preferably in a range of from 30 to 100° C. After completion of the reaction, the reaction products can be neutralized with an acid or an alkali. Illustrative of the acid include inorganic acids such as sulfuric acid, hydrochloric acid and phosphoric acid, and organic acids such as acetic acid. Illustrative of the alkali include hydroxides of Group 1 or Group 2 elements, such as sodium hydroxide, potassium hydroxide and magnesium hydroxide. Alternatively, a subsequent reaction may be conducted without such neutralization.

(Sulfonation Reaction)

The sulfonation reaction of a polysaccharide or a derivative thereof is conducted by dissolving or dispersing the polysaccharide or derivative thereof in a suitable solvent and reacting it with a sulfonating agent (b).

In the sulfonating agent (b), the substituted halogen atom(s) in the $C_{1-5}$ haloalkanesulfonic acid which may be substituted with hydroxyl groups include fluorine atom(s), chlorine atom(s), bromine atom(s) and/or the like. Illustratives of the salt of the $C_{1-5}$ haloalkanesulfonic acid are its salts with Group 1 or Group 2 elements, such as the sodium salt, potassium salt, calcium salt and magnesium salt; and its ammonium salt. Preferred examples of the sulfonating agent include vinylsulfonic acids, 3-halo-2-hydroxypropanesulfonic acids, 3-halopropanesulfonic acids, and 2,3-epoxypropanesulfonic acid. These sulfonating agents can be used either singly or in combination of two or more thereof. The amount of the sulfonating agent can be optionally adjusted depending upon the desired amount of sulfoalkyl groups (B) to be introduced into the polysaccharide or its derivative. In general, however, it is preferred to use the sulfonating agent in an amount of from 0 to 10 equivalents, especially from 0 to 2 equivalents per constituent monosaccharide residual group of the polysaccharide or its derivative.

The sulfonation reaction is preferably conducted in the presence of an alkali as needed. Examples of the alkali include hydroxides, carbonates and bicarbonates of Group 1 or Group 2 elements, with sodium hydroxide, potassium hydroxide, calcium hydroxide and magnesium hydroxide being preferred. Use of the alkali in an amount of from 0.1 to 3.0 molar times, especially from 0.5 to 1.5 molar times of the sulfonating agent provides good results and is preferred.

Examples of the solvent include lower alcohols, for example, isopropyl alcohol and tert-butyl alcohol. In order to enhance the reactivity between the polysaccharide or its derivative and the sulfonating agent, a mixed solvent obtained by adding 0.1 to 100 wt. %, more preferably 1 to 50 wt. % of water to a lower alcohol can also be used.

The reaction temperature is preferably in a range of from 0 to 150° C., particularly preferably from 30 to 100° C. After completion of the reaction, the alkali can be neutralized with an acid. Illustrative of the acid are inorganic acids such as sulfuric acid, hydrochloric acid and phosphoric acid, and organic acids such as acetic acid. Alternatively, a subsequent reaction may be conducted without such neutralization.

(Carboxylation Reaction)

The carboxylation reaction of a polysaccharide or a derivative thereof is conducted by dissolving or dispersing the polysaccharide or derivative thereof in a suitable solvent and reacting it with a carboxylating agent (c) in the presence of an alkali.

Specific examples of the carboxylating agent (c) include monochloroacetic acid, sodium monochloroacetate, potassium monochloroacetate, sodium monobromoacetate, and potassium monobromoacetate. These carboxylating agents can be used either singly or in combination of two or more thereof. The amount of the carboxylating agent can be optionally adjusted depending upon the desired amount of carboxyalkyl groups (C) introduced into the polysaccharide or its derivative. In general, however, it is preferred to use the carboxylating agent in an amount of from 0 to 10 equivalents, especially from 0 to 1 equivalent per constituent monosaccharide residual group of the polysaccharide or its derivative.

Examples of the alkali used in this reaction include sodium hydroxide, potassium hydroxide, calcium hydroxide and magnesium hydroxide. Use of an alkali in an amount of from 0.1 to 3.0 molar times, especially from 1.05 to 2.5 molar times of the carboxylating agent is preferred. Use of too small amount of the alkali lowers reaction velocity, while use of too much amount of the alkali tends to cause decomposition or the like of the polysaccharide or its derivative. Therefore, it is not desired to use the alkali in an amount outside the above-described range.

Examples of the solvent include isopropyl alcohol and tert-butyl alcohol. In general, a mixed solvent obtained by adding 1 to 50 wt. % of water to isopropyl alcohol or tert-butyl alcohol is used to enhance the reactivity between the polysaccharide or its derivative and the carboxylating agent (c).

The reaction temperature is preferably in a range of from 0 to 150° C., particularly preferably in a range of from 30 to 100° C. After completion of the reaction, the alkali can be neutralized with an acid. Illustrative of the acid are inorganic acids such as sulfuric acid, hydrochloric acid and phosphoric acid, and organic acids such as acetic acid. Alternatively, a subsequent reaction may be conducted without such neutralization.

(Cationization Reaction)

The cationization reaction of a polysaccharide or a derivative thereof is conducted by dissolving or dispersing the polysaccharide or derivative in a suitable solvent and reacting it with a cationizing agent (d).

Among the groups represented by $D^2$ in the formula (4), the epoxylated $C_{3-6}$ alkyl group includes 2,3-epoxypropyl, 3,4-epoxybutyl, 4,5-epoxypentyl, 5,6-epoxyhexyl and the like. The linear or branched, halogenated $C_{1-6}$ alkyl group which may substituted with one or more hydroxyl groups can be 2-chloroethyl, 3-chloropropyl, 4-chlorobutyl, 6-chlorohexyl, 2-bromoethyl, 2-hydroxy-3-chloropropyl, 1-hydroxymethyl-2-chloroethyl, or the like. Preferred examples of $D^2$ include 2,3-epoxypropyl, 2-chloroethyl, 3-chloropropyl, and 2-hydroxy-3-chloropropyl. These cationizing agents (d) can be used either singly or in combination of two or more thereof. The amount of the cationizing agent can be optionally adjusted depending upon the desired introduction degree of cationic substituent groups (D) into the polysaccharide or its derivative. In general, however, it is preferred to use the cationizing agent in an amount of from 0 to 10 equivalents, especially from 0 to 5 equivalents per constituent monosaccharide residual group of the polysaccharide or its derivative.

This reaction may be preferably conducted in the presence of an alkali as needed. Examples of the alkali include hydroxides, carbonates and bicarbonates of Group 1 or Group 2 elements, with sodium hydroxide, potassium hydroxide, calcium hydroxide and magnesium hydroxide being preferred. Use of an alkali in an amount of from 1.0 to 3.0 molar times, especially from 1.05 to 1.5 molar times of the cationizing agent (d) provides good results and thus is preferred.

Examples of the solvent include lower alcohols, for example, isopropyl alcohol and tert-butyl alcohol. In order to enhance the reactivity between the polysaccharide or its derivative and the cationizing agent (d), it is possible to use a mixed solvent obtained by adding 0.1 to 100 wt. %, more preferably 1 to 50 wt. % of water to a lower alcohol.

The reaction temperature is preferably in a range of from 0 to 150° C., particularly preferably in a range of from 30 to 100° C. After completion of the reaction, the alkali can be neutralized using an acid. Illustrative of the acid includes inorganic acids such as sulfuric acid, hydrochloric acid and phosphoric acid, and organic acids such as acetic acid. Alternatively, a subsequent reaction may be conducted without such neutralization.

If the polysaccharide derivative obtained by any one of the above reactions is subsequently subjected to one of the other reactions, the polysaccharide derivative can be used without neutralization, or, as nessesary, after removing the unreacted compound (a), (b), (c) or (d) and salts by-produced by neutralization or the like, by means of separation through filtration or by washing the reaction products with hot water, water-containing isopropyl alcohol, water-containing acetone or the like. After completion of the introduction of the desired substituent groups, the polysaccharide derivative according to the present invention can be obtained by neutralizing the reaction liquid, separating the reaction product by filtration or the like, washing the reaction product, as necessary, and then drying.

The polysaccharide derivative of the present invention thus obtained is excellent in water solubility, and exhibits such Theological characteristic that the viscosity increases at a high temperature. It is, therefore, useful as a thickener having an excellent handling property at low temperatures and having a sufficient thickening property at a high temperature, and also useful as an emulsifier having an excellent emulsifying action which allows highly stable co-existence of hydrophobic compounds in water. Accordingly, an aqueous composition containing the polysaccharide derivative according to the present invention, when a hydrophobic compound exists in the aqueous composition, allows the hydrophobic compound to exist extremely stable owing to the emulsifying action, dispersing action and protective colloid action of the polysaccharide derivative.

The aqueous polysaccharide composition containing the hydrophobic compound does not change over days or, even by the addition or the like of a commonly used surfactant, undergoes neither change in viscosity nor change in external appearance such as separation. Moreover, the composition efficiently releases the hydrophobic compound when the product containing the composition is used. It is, therefore, extremely useful in the field of toiletry.

Examples of the hydrophobic compound include higher alcohols, sterols, silicones, fluorine-containing oils, oil components and the like, which are added to increase the function and additional value of toiletry products.

Examples of the higher alcohols include benzyl alcohol, isocetyl alcohol, isostearyl alcohol, behenyl alcohol, hexadecyl alcohol, phenylethyl alcohol, cetanol, stearyl alcohol, oleyl alcohol, 2-octyldodecanol, batyl alcohol, and 2-hexyldecanol, with cetanol and stearyl alcohol being particularly preferred.

Examples of the sterols include cholesterol, cholesteryl isostearate, provitamin $D_3$, campesterol, stegmastanol, stegmasterol, 5-dihydrocholesterol, α-spinasterol, palesterol, clionasterol, γ-citosterol, stegmastenol, sargasterol, apenasterol, ergostanol, citosterol, colbisterol, chondrillasterol, polyferrasterol, haliclonasterol, neospongosterol, fucosterol, aptostanol, ergostadienol, ergosterol, 22-dihydroergosterol, brassicasterol, 24-methylenecholesterol, 5-dihydroergosterol, dehydroergosterol, fungisterol, cholestanol, coprostanol, zymosterol, 7-ketocholesterol, latosterol, 22-dehydrocholesterol, β-citosterol, cholestatrien-3β-ol, coprostanol, cholestanol, ergosterol, 7-dehydrocholesterol, 24-dehydrocholestadion-3β-ol, equilenin, equilin, estron, 17β-estradiol, androst-4-ene-3β, 17β-diol, dehydroepiandrosterone, and cholesteryl alkenylsuccinates (JP-A-5-294989). Among these, cholesterol, cholesteryl isostearate and cholesteryl alkenylsuccinates are particularly preferred.

Examples of the silicones include those commonly used in toiletry products, for example, octamethylpolysiloxane, tetradecamethylpolysiloxane, methylpolysiloxane, highly-polymerized methylpolysiloxane and methylphenylpolysiloxane, and also include methylpolysiloxanes such as octamethylcyclotetrasiloxane and decamethylcyclopentanesiloxane; trimethylsiloxysilicate; and modified silicones such as alkyl-modified silicones, polyether- and alkyl-modified silicones, amino-modified silicones, fluorine-modified silicones, alkyl-glyceryl-ether-modified silicones, and modified organopolysiloxanes as disclosed in JP-A-6-72851.

The fluorine-containing oils are preferably perfluoropolyethers, i.e. perfluoro-organic compounds which are liquid at room temperature, or fluorine-modified silicones, such as, for example, perfluorodecalin, perfluoroadamantane, perfluorobutyltetrahydrofuran, perfluorooctane, perfluorononane, perfluoropentane, perfluorodecane, perfluorododecane, and perfluoropolyethers.

The oil components may be either volatile or non-volatile. Illustrative of the oil components are hydrocarbons such as solid or liquid paraffin, vaseline, crystal oil, ceresin, ozokerite, montan wax, squalane, and squalene; Eucalyptus oil, peppermint oil, camellia oil, macadamia nut oil, avocado oil, beef tallow, lard, horse grease, yolk oil, olive oil, carnauba wax, lanolin, and jojoba oil; ester oils such as glyceryl monostearate, glyceryl distearate, glyceryl monooleate, isopropyl palmitate, isopropyl stearate, butyl stearate, isopropyl myristate, neopentyl glycol dicaprylate, diethyl phthalate, myristyl lactate, diisopropyl adipate, cetyl myristate, myristyl lactate, diisopropyl adipate, cetyl myristate, cetyl lactate, 1-isostearolyl-3-myristoylglycerol, cetyl 2-ethylhexanoate, 2-ethlhexyl palmitate, 2-octyldecyl myristate, neopentyl glycol di(2-ethylhexanoate), 2-octyldodecyl oleate, glyceryl triisostearate, and glyceryl di(p-methoxycinnamate)-mono(2-ethylhexanoate); higher fatty acids such as stearic acid, palmitic acid, and oleic acid; natural essential oils such as rosemary, rooibos, royal jelly, and witch-hazel leave oil; and functional oil substances such as lignan, vitamin E, oil-soluble vitamin C, vitamin A derivatives, ceramides, structurally ceramide analogous substances, oil-soluble ultraviolet absorbers and perfumes.

The content of the polysaccharide derivative in the aqueous composition is preferably 0.01 to 5 wt. %, more preferably 0.05 to 2 wt. %. When a hydrophobic compound is added to the composition, its content is preferably 0.0001 to 50 wt. %, and more preferably 0.001 to 30 wt. % of the composition.

The polysaccharide-containing aqueous composition according to the present invention can be optionally incorporated with surfactants, dispersants, solvents, perfumes, dyes, inorganic salts, pH adjusters and the like which are conventionally used in toiletry products.

The polysaccharide and the polysaccharide-containing aqueous composition according to the present invention can be used for various toiletry products such as bath preparations, massaging cosmetic preparations, shower preparations, skin care preparations, hair washing preparations, body washing preparations, garment detergents, garment finishing agents and hard surface cleansers.

EXAMPLES

In the following Examples, the degree of substitution with substituent groups (A) in the polysaccharide derivative according to the present invention was determined by Zeisel method [D. G. Anderson, Anal. Chem., 43, 894 (1971)], while the degree of substitution with each of sulfoalkyl groups (B), carboxyalkyl groups (C) and cationic substituent groups (D) in the polysaccharide derivative according to the present invention was determined by the colloidal titration method. Incidentally, the term "degree of substitution" used in the following examples indicates an average number of substituent groups per constituent monosaccharide residual group.

Example 1

Hydroxyethylcellulose having a weight average molecular weight of about 800,000 and a degree of substitution with hydroxyethyl groups of 1.8 ("HEC-QP15000H", product of Union Carbide Corp.)(80 g), isopropyl alcohol (640 g) and p-toluenesulfonic acid (2.0 g) were mixed to prepare a slurry, followed by stirring at room temperature for 30 minutes under a nitrogen gas atmosphere. To the solution, a compound (15 g) represented by the following formula:

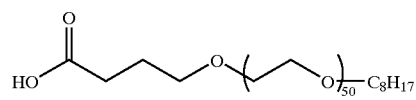

was added, and a reaction was conducted at 80° C. for 8 hours to effect polyoxyalkylation. After completion of the reaction, the reaction mixture was neutralized with a 48% aqueous solution of sodium hydroxide, and the reaction product was collected by filtration. The reaction product was washed twice with 80% isopropyl alcohol (500 g) and twice with isopropyl alcohol (500 g), and dried overnight at 70° C. under reduced pressure to afford a hydroxyethylcellulose derivative (Invention Compound 1)(73.4 g).

The degree of substitution with polyoxyalkylene-containing substituent groups in the resultant hydroxyethylcellulose derivative was 0.010.

Example 2

Potato starch (product of Katayama Chemical Industries Co., Ltd.)(80 g), 50% isopropyl alcohol (640 g) and a 48% aqueous solution of sodium hydroxide (5.5 g) were mixed to prepare a slurry, followed by stirring at room temperature for 30 minutes under a nitrogen gas atmosphere. To the solution, a compound (19.0 g) represented by the following formula:

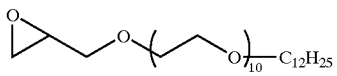

was added, and a reaction was conducted at 80° C. for 8 hours to effect polyoxyalkylation. After completion of the reaction, the reaction mixture was neutralized with acetic acid, and the reaction product was collected by filtration. The reaction product was washed twice with 50% isopropyl alcohol (500 g) and then twice with acetone (500 g), and dried overnight at 70° C. under reduced pressure to afford a polyoxyalkylated starch derivative (Invention Compound 2)(69.4 g).

The degree of substitution with polyoxyalkylene-containing substituent groups in the resultant starch derivative was 0.005.

Example 3

To the polyoxyalkylated starch derivative (20.0 g) obtained in Example 2, 70% isopropyl alcohol (200 g), sodium 3-chloro-2-hydroxypropanesulfonate (42.6 g) and a 48% aqueous solution of sodium hydroxide (18.0 g) were added, followed by sulfonation at 50° C. for 5 hours. After completion of the reaction, the reaction mixture was neutralized with acetic acid, and the reaction product was collected by filtration. The reaction product was washed thrice with 70% isopropyl alcohol (400 g) and twice with isopropyl alcohol (300 g), and dried overnight at 70° C. under reduced pressure to afford a polyoxyalkylated and sulfonated starch derivative (Invention Compound 3)(38.3 g).

The degree of substitution with 3-sulfo-2-hydroxypropyl groups in the resultant starch derivative was 0.301.

Example 4

The polyoxyalkylated starch derivative (35.5 g) obtained in Example 2, 70% isopropyl alcohol (350 g) and a 48% aqueous solution of sodium hydroxide (2.4 g) were mixed to prepare a slurry, followed by stirring at room temperature for 30 minutes under a nitrogen gas atmosphere. To the reaction mixture, sodium monochloroacetate (25.1 g) and a 48% aqueous solution of sodium hydroxide (18.0 g) were added, and carboxymethylation was conducted at 50° C. for 5 hours. After completion of the reaction, the reaction mixture was neutralized with acetic acid, and the reaction product was collected by filtration. The reaction product was washed thrice with 70% isopropyl alcohol (400 g) and twice with isopropyl alcohol (300 g), and dried overnight at 70° C. under reduced pressure to afford a polyoxyalkylated and carboxymethylated starch derivative (Invention Compound 4)(33.8 g). The degree of carboxymethylation of the resultant starch derivative was 0.48.

Example 5

The polyoxyalkylated starch derivative (35.5 g) obtained in Example 2, 70% isopropyl alcohol (350 g) and a 48% aqueous solution of sodium hydroxide (2.4 g) were mixed to prepare a slurry, followed by stirring at room temperature for 30 minutes under a nitrogen gas atmosphere. To the reaction mixture, a 60% aqueous solution of (3-chloro-2-hydroxypropyl)-trimethyl ammonium chloride (7.0 g) and a 48% aqueous solution of sodium hydroxide (2.0 g) were added, and cationization was conducted at 50° C. for 1 hour. After completion of the reaction, the reaction mixture was neutralized with acetic acid, and the reaction product was collected by filtration. The reaction product was washed thrice with 70% isopropyl alcohol (400 g) and twice with isopropyl alcohol (300 g), and dried overnight at 70° C. under reduced pressure to afford a polyoxyalkylated and cationized starch derivative (Invention Compound 5)(34.2 g). The degree of cationization of the resultant starch derivative was 0.10.

Example 6

Hydroxyethylcellulose having a weight average molecular weight of 1,500,000 and a degree of substitution with hydroxyethyl groups of 1.8 ("HEC-QP100MH", product of Union Carbide Corp.) (80 g), 80% isopropyl alcohol (640 g) and a 48% aqueous solution of sodium hydroxide (5.34 g) were mixed to prepare a slurry, followed by stirring at room temperature for 30 minutes under a nitrogen gas atmosphere. To the solution, a compound (12.78 g) represented by the following formula:

was added, and a reaction was conducted at 80° C. for 8 hours to effect polyoxyalkylation. After completion of the reaction, the reaction mixture was neutralized with acetic acid, and the reaction product was collected by filtration. The reaction product was washed twice with isopropyl alcohol (500 g), and dried overnight at 60° C. under reduced pressure to afford a polyoxyalkylated hydroxyethylcellulose derivative (Invention Compound 6)(72.0 g).

The degree of substitution by polyoxyalkylene-containing substituent groups in the resultant hydroxyethylcellulose derivative was 0.004.

Example 7

Hydroxyethylcellulose having a weight average molecular weight of 1,500,000 and a degree of substitution with hydroxyethyl groups of 1.8 ("HEC-QP100MH", product of Union Carbide Corp.) (80 g), 80% isopropyl alcohol (640 g) and a 48% aqueous solution of sodium hydroxide (5.34 g) were mixed to prepare a slurry, followed by stirring at room temperature for 30 minutes under a nitrogen gas atmosphere. To the solution, a compound (21.7 g) represented by the following formula:

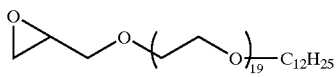

was added, and a reaction was conducted at 80° C. for 8 hours to effect polyoxyalkylenization. After completion of the reaction, the reaction mixture was neutralized with acetic acid, and the reaction product was collected by filtration. The reaction product was washed twice with isopropyl alcohol (500 g), and dried overnight at 60° C. under reduced pressure to afford a polyoxyalkylenized hydroxyethylcellulose derivative (Invention Compound 7)(74.0 g).

The degree of substitution by polyoxyalkylene-containing substituent groups in the resultant hydroxyethylcellulose derivative was 0.004.

Example 8

Hydroxyethylcellulose having a weight average molecular weight of 800,000 and a degree of substitution by hydroxyethyl groups of 1.8 (80 g; "HEC-QP15000H", product of Union Carbide Corp.), 80% isopropyl alcohol (640 g) and a 48% aqueous solution of sodium hydroxide (5.34 g) were mixed to prepare a slurry, followed by stirring at room temperature for 30 minutes under a nitrogen gas atmosphere. To the solution, a compound (13.7 g) represented by the following formula:

was added, and a reaction was conducted at 80° C. for 8 hours to effect polyoxyalkylation. After completion of the reaction, the reaction mixture was neutralized with acetic acid, and the reaction product was collected by filtration. The reaction product was washed twice with isopropyl alcohol (500 g), and dried overnight at 60° C. under reduced pressure to afford a polyoxyalkylated hydroxyethylcellulose derivative (Invention Compound 8)(69.0 g).

The degree of substitution with polyoxyalkylene-containing substituent groups in the resultant hydroxyethylcellulose derivative was 0.003.

Comparative Example 1

Hydroxyethylcellulose having a weight average molecular weight of about 800,000 and a degree of substitution with hydroxyethyl groups of 1.8 ("HEC-QP15000H", product of Union Carbide Corp.) was used as Comparative Compound 1.

Comparative Example 2

Methylcellulose having a weight average molecular weight of about 300,000 and a degree of substitution with methoxy groups of 1.8 ("SM-1500", product of Shin-Etsu Chemical Co., Ltd.) was used as Comparative Compound 2.

Comparative Example 3

Hydroxyethylcellulose having a weight average molecular weight of 1,500,000 and a degree of substitution by hydroxyethyl groups of 1.8 (80 g; "HEC-QP100MH", product of Union Carbide Corp.), 80% isopropyl alcohol (640 g) and a 48% aqueous solution of sodium hydroxide (5.34 g) were mixed to prepare a slurry, followed by stirring at room temperature for 30 minutes under a nitrogen gas atmosphere. To the solution, a compound (4.8 g) represented by the following formula:

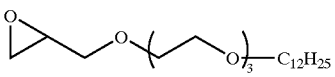

was added, and a reaction was conducted at 80° C. for 8 hours to effect polyoxyalkylation. After completion of the reaction, the reaction mixture was neutralized with acetic acid, and the reaction product was collected by filtration. The reaction product was washed twice with isopropyl alcohol (500 g), and dried overnight at 60° C. under reduced pressure to afford a polyoxyalkylated hydroxyethylcellulose derivative (Comparative Compound 3)(72.3 g).

The degree of substitution with polyoxyalkylene-containing substituent groups in the resultant hydroxyethylcellulose derivative was 0.004.

Test 1 (Thickening Property Test)

Invention compounds (1.0 g) and comparative compounds (4.0 g) were separately dissolved under stirring in 200-mL aliquots of deionized water. After the resultant aqueous solutions were allowed to stand overnight at room temperature, their viscosities were measured at solution temperatures of 10° C. and 60° C., respectively. Those viscosities were measured using a Brookfield viscometer (12 rpm). The results are shown in Table 1.

TABLE 1

|  | Viscosity of aqueous Solution (mPa · s) | |
|---|---|---|
|  | 10° C. | 60° C. |
| Invention Compound 1 | 420 | 2300 |
| Invention Compound 2 | 6500 | 12000 |
| Invention Compound 3 | 6000 | 10500 |
| Invention Compound 4 | 5400 | 9300 |
| Invention Compound 5 | 6300 | 9800 |
| Comparative Compound 1 | 20000 | 1600 |
| Comparative Compound 2 | 2500 | 400 |

The polysaccharide derivatives according to the present invention afforded aqueous solutions of high clarity and had an excellent thickening property at high temperatures as apparent from Table 1.

Test 2 (Emulsion Stability Test)

An aqueous composition was prepared by gradually adding ion-exchange water with stirring to a dispersion of polysaccharides and oil or to a dispersion of polysaccharides, glycerin and oil.

An aqueous composition incorporated with a surfactant was prepared by adding the surfactant to the above-described dispersion.

The resultant aqueous compositions were stored at room temperature and 40° C. for one month, and were evaluated with regard to stability (occurrence or non-occurrence of separation). The results are shown in Table 2.

TABLE 2

(wt. %)

|  | Invention product | | | | | | | | Comparative product | | | |
|---|---|---|---|---|---|---|---|---|---|---|---|---|
|  | 1 | 2 | 3 | 4 | 5 | 6 | 7 | 8 | 1 | 2 | 3 | 4 |
| Invention Compound 6 | 0.5 | 0.5 | 0.5 | 0.5 |  |  |  |  |  |  |  |  |
| Invention Compound 7 |  |  |  |  | 0.5 | 0.5 | 0.5 | 0.5 |  |  |  |  |
| Comparative Comp'd 3 |  |  |  |  |  |  |  |  |  |  | 0.5 | 0.5 |

TABLE 2-continued

|  | Invention product | | | | | | | | Comparative product | | | | (wt. %) |
| --- | --- | --- | --- | --- | --- | --- | --- | --- | --- | --- | --- | --- | --- |
|  | 1 | 2 | 3 | 4 | 5 | 6 | 7 | 8 | 1 | 2 | 3 | 4 | |
| 86% Glycerin |  | 9.5 |  | 9.5 |  | 9.5 |  | 9.5 |  | 9.5 |  | 9.5 | |
| Silicone oil ("KP96A 6CS", product of Shin-Etsu Silicone Co., Ltd.) |  |  | 5 |  |  |  | 5 |  | 5 |  | 5 |  | |
| Squalane | 5 |  |  |  | 5 |  |  |  |  |  |  |  | |
| Sunflower oil |  |  | 5 |  |  | 5 |  |  | 5 |  | 5 |  | |
| Glyceryl myristate/Isostearate |  | 5 |  |  |  | 5 |  |  |  |  |  |  | |
| Potassium laurate |  |  | 15 |  |  |  | 15 |  | 15 |  | 15 |  | |
| Polyoxyethylene lauryl sulfate |  |  |  | 15 |  |  |  | 15 |  | 15 |  | 15 | |
| Deionized water | Balance | Balance | Balance | Balance | Balance | Balance | Balance | Balance | Balance | Balance | Balance | Balance | |
| Stability (room temp., 1 month) | Good | Good | Good | Good | Good | Good | Good | Good | Separated | Separated | Separated | Separated | |
| Stability (40° C., 1 month) | Good | Good | Good | Good | Good | Good | Good | Good | Separated | Separated | Separated | Separated | |

From Table 2, the polysaccharide derivatives according to the present invention emulsified the hydrophobic compounds sufficiently, and the resulting compositions had good stability. It is also appreciated that their stability was not impaired even by the existence of the surfactant.

Example 9

(Bath Preparation)

The ingredients in Table 3 were combined into a uniform mixture by a Henschel mixer to give a powder-form bath preparation.

TABLE 3

| Ingredient | Mixed amount (wt. %) |
| --- | --- |
| Invention Compound 1 | 90 |
| Sodium hydrogencarbonate | 8 |
| Polyethylene glycol 6000 (powder) | 1.9 |
| Color additive | 0.1 |

When the resultant powder-form bath preparation (200 g) was dissolved in bathwater (180 L), the bathwater viscosity at a bathwater temperature of 40° C. was 160 mPa·s. When the bathwater temperature dropped to 25° C., the viscosity of the bathwater decreased to 20 mPa·s, thereby permitting smooth drainage of the bathwater. It was also possible to use the bathwater as washing water in a fully automatic washing machine without any problem.

Example 10

(Shampoo)

Using Invention Compound 6, a shampoo of the following formulation was produced.

| (Formulation) | (wt. %) |
| --- | --- |
| Polyoxyethylene alkyl sulfate | 15.0 |
| Isopropyl palmitate | 5.0 |
| Invention Compound 6 | 0.5 |
| Lauroyl diethanolamide | 3.0 |
| Lauryl dimethyl amine oxide | 0.5 |
| Hydroxyethylcellulose (product of Daicel Chemical Industries, Ltd.) | 0.1 |
| Sodium benzoate | 0.3 |
| Color additive | appropriate amount |
| Fragrance | appropriate amount |
| Citric acid | appropriate amount |
| Water | balance |
| Total | 100.0 |

Comparative Example 4

A shampoo was produced as in Example 10 except that Invention Compound 6 was not used.

Compared with the shampoo of Comparative Example 4, the shampoo of Example 10 was better in foaming power and cleansing power and was also better in touch feel during rinsing and after drying.

Example 11

(Body Shampoo)

Using Invention Compound 7, a body shampoo of the following formulation was produced.

| (formulation) | (wt. %) |
| --- | --- |
| Potassium monolauryl phosphate | 15.0 |
| Glyceryl triisostearate | 5.0 |
| Invention Compound 7 | 0.5 |
| Polyoxyethylene (EO3) lauryl glucoside | 5.0 |
| Lauryl dimethylamine oxide | 3.0 |
| Glycerin | 4.0 |
| Sucrose fatty acid ester | 1.0 |
| Methylparaben | 0.3 |
| Color additive | appropriate amount |
| Fragrance | appropriate amount |
| Citric acid | appropriate amount |
| Water | Balance |
| Total | 100.0 |

Comparative Example 5

A body shampoo was produced as in Example 11 except that Invention Compound 7 was not used.

Compared with the body shampoo of Comparative Example 5, the body shampoo of Example 11 was better in foaming power and cleansing power and, after washing, gave moist and good touch feel.

Example 12
(Milky Lotion)

Using Invention Compound 7, a milky lotion was prepared with the following formulation. Compared with a milky lotion of Comparative Example 6, the milky lotion of this example was better in stability and was non-sticky, and gave a better feeling of use.

| (Formulation) | (wt. %) |
| --- | --- |
| Squalane | 5.0 |
| Olive oil | 8.0 |
| Jojoba oil | 1.0 |
| Polyoxyethylene hydrogenated castor oil (10EO) | 1.0 |
| Sorbitan monostearate | 1.0 |
| Invention Compound 7 | 0.5 |
| Butylparaben | 0.1 |
| Methylparaben | 0.1 |
| Ethanol | 5.0 |
| Glycerin | 3.0 |
| Fragrance | 0.05 |
| Water | Balance |
| Total | 100.0 |

Comparative Example 6

A milky lotion was formulated as in Example 12 except that Invention Compound 7 was not used.

Example 13
(Lotion)

Using Invention Compound 7, a lotion was prepared with the following formulation. Compared with a lotion of Comparative Example 7, the lotion of this example was better in stability and gave a better feeling of use.

| (Formulation) | (wt. %) |
| --- | --- |
| Ethanol | 5.0 |
| Glycerin | 3.0 |
| Polyethylene glycol 1500 | 4.0 |
| Polyoxyethylene oleyl ether (20EO) | 0.3 |
| Polyoxyethylene hydrogenated castor oil (30EO) | 0.2 |
| Polysaccharide derivative (Invention Compound 7) | 0.15 |
| Zinc p-phenolsulfonate | 0.2 |
| Water | Balance |
| Total | 100.0 |

Comparative Example 7

A lotion was formulated as in Example 13 except tha Invention Compound 7 was not used.

Example 14
(Garment Softener)

Using Invention Compound 7, a garment softener was prepared with the following formulation. Compared with a garment softener of Comparative Example 8, the garment softener of this example was better in stability and gave a better feeling after drying of the garment. Further, a fragrance smell from dried garment was strong.

| (Formulation) | (wt. %) |
| --- | --- |
| Dioleoylethyl dimethyl ammonium chloride | 15.0 |
| Invention Compound 7 | 0.5 |
| Amino-modified silicone | 5.0 |
| Polyoxyethylene lauryl ether (m = 21) | 2.0 |
| Glycerin | 1.0 |
| Calcium chloride | appropriate amount |
| Fragrance | 0.3 |
| Water | Balance |
| Total | 100.0 |

Comparative Example 8

The garment softener was formulated as in Example 14 except that Invention Compound 7 was not used.

Example 15
(Liquid Detergent for Garment)

Using Invention Compound 7, a liquid detergent for garment was prepared with the following formulation. Compared with a liquid detergent for garment of Comparative Example 9, the liquid detergent for garment of this example was better in detergency and stability and gave a better feeling after drying of the garment.

| (Formulation) | (wt. %) |
| --- | --- |
| Nonionic surfactant ($C_{10-14}$ monohydric alcohol block added with 5 moles of EO, 2 moles of PO and 5 moles of EO, respectively in average) | 5.0 |
| Nonionic surfactant ($C_{10-14}$ dihydric alcohol block added with 8 moles of EO and 1 mole of PO, respectively in average) | 30 |
| LAS-S agent | 1.5 |
| Na salt of $C_{12-14}$ fatty acid | 1.0 |
| Invention Compound 7 | 0.5 |
| Amino-modified silicone | 5.0 |
| Polyoxyethylene glycol phenyl ether | 5.0 |
| Diethanolamine | 8.0 |
| Propylene glycol | 6.0 |
| Ethanol | 2.0 |
| Sodium sulfite | 0.3 |
| Fragrance | appropriate amount |
| NaOH | an amount sufficient to adjust the pH of the concentrate to 10.5 |
| Water | Balance |
| Total | 100.0 |

Comparative Example 9

The liquid detergent for garment was formulated as n Example 15 except that Invention Compound 7 was not used.

Industrial Applicability

The polysaccharide derivatives of the present invention are excellent in water solubility and have such a rheological characteristic that the viscosity thereof increases at a higher temperature. Thus, the polysaccharide derivatives of the invention are very useful as a thickener which exhibits an excellent handling property at low temperatures and a sufficient thickening effect at high temperatures, as an emulsifier which exhibits an excellent emulsifying action allowing hydrophobic compounds to exist very stably in water, and also as a thickening and stabilizing agent for various toiletry products such as viscous bath preparation massaging cosmetic preparations, shower preparations, skin care preparations, hair washing preparations, body washing preparations, garment detergents, garment finishing agents and hard surface cleaning agents.

What is claimed is:

1. A polysaccharide derivative comprising a polysaccharide, or a derivative thereof, wherein a part or all of the hydrogen atoms of the hydroxyl groups of the polysaccharide, or the derivative thereof, are replaced with substituent group (A)

(A) a group represented by the following formula:

—E$^1$—(OA)$_n$—E$^2$—R    (1)

wherein E$^1$ represents a linear or branched, divalent, saturated C$_{1-6}$ hydrocarbon group which may be substituted with one or more hydroxyl groups or oxo groups, n represents a number of from 8 to 300, n numbers of As may be the same or different and each independently represents a linear or branched, divalent, saturated C$_{1-6}$ hydrocarbon group, E$^2$ represents an ether bond or an oxycarbonyl group (—OCO— or —COO—), and R represents a linear or branched C$_{4-30}$ alkyl group which may be substituted with one or more hydroxyl groups, wherein, the hydrogen atom(s) of one or more hydroxy groups in said substituent groups (A) may be further replaced with said substituent groups (A);

and wherein the degree of substitution of the polysaccharide, or the derivative thereof, with the substituent group (A) is 0.0005 to 0.5 per constituent monosaccharide residual group.

2. A polysaccharide derivative comprising a polysaccharide, or a derivative thereof, wherein a part or all of the hydrogen atoms of the hydroxyl groups of the polysaccharide, or the derivative thereof, are replaced with substituent group (A)

(A) a group represented by the following formula:

—E$^1$—(OA)$_n$—E$^2$—R    (1)

wherein E$^1$ represents a linear or branched, divalent, saturated C$_{1-6}$ hydrocarbon group which may be substituted with one or more hydroxyl groups or oxo groups, n represents a number of from 8 to 300, n numbers of as may be the same or different and each independently represents a linear or branched, divalent, saturated C$_{1-6}$ hydrocarbon group, E$^2$ represents an ether bond or an oxycarbonyl group (—OCO— or —COO—), and R represents a linear or branched C$_{4-30}$ alkyl group which may be substituted with one or more hydroxyl groups, wherein, the hydrogen atom(s) of one or more hydroxy groups in said substituent groups (A) may be further replaced with said substituent groups (A); and wherein a part or all of the hydrogen atoms of the hydroxyl groups in the polysaccharide derivative are further replaced with one or more substituent groups selected from the group consisting of substituent group (B), substituent group (C) and substituent group (D):

(B) a C$_{1-5}$ sulfoalkyl group or salt thereof, each of which may be substituted with one or more hydroxyl groups, (C) a C$_{2-6}$ carboxyalkyl group or salt thereof, each of which may be substituted with one or more hydroxyl groups, and (D) a group represented by the following formula (2):

wherein D$^1$ represents a linear or branched, divalent, saturated C$_{1-6}$ hydrocarbon group which may be substituted with one or more hydroxyl groups R$^1$, R$^2$ and R$^3$ may be the same or different and each independently represent a linear or branched C$_{1-3}$ alkyl group which may be substituted with one or more hydroxyl groups and X— represents hydroxyl ion, a halogen ion or an organic acid ion.

3. A process for the production of the polysaccharide derivative as defined in claim 1, which comprises reacting a polysaccharide or a derivative thereof with a polyoxyalkylating agent (a) represented by the following formula (3):

E$^3$—(OA)$_n$—E$^2$—R    (3)

wherein E$^3$ represents an epoxylated C$_{3-6}$ alkyl group, a halogenated, linear or branched C$_{1-6}$ alkyl group which may be substituted with one or more hydroxyl groups, or a carboxyl or C$_{2-6}$ carboxyalkyl group or a derivative thereof, and n stands for a number of from 8 to 300, n numbers of As may be the same or different and each independently represent a linear or branched, divalent, saturated C$_{1-6}$ hydrocarbon group, E$^2$ represents an ether bond or an oxycarbonyl group (—OCO— or —COO—), and R represents a linear or branched C$_{4-30}$ alkyl group which may be substituted with one or more hydroxyl groups.

4. A process for the production of the polysaccharide derivative as defined in claim 2, which comprises reacting a polysaccharide or a derivative thereof with (a) a polyoxyalkylenizing agent represented by the following formula (3):

E$^3$—(OA)$_n$—E$^2$—R    (3)

wherein E$^3$ represents an epoxylated C$_{3-6}$ alkyl group, a halogenated linear or branched C$_{1-6}$ alkyl group which may be substituted with one or more hydroxyl groups, or a carboxyl or C$_{2-6}$ carboxyalkyl group or a derivative thereof, and n stands for a number of from 8 to 300, n numbers of As may be the same or different and each independently represent a linear or branched, divalent, saturated C$_{1-6}$ hydrocarbon group, E$^2$ represents an ether bond or an oxycarbonyl group (—OCO— or —COO—), and R represents a linear or branched C$_{4-30}$ alkyl group which may be substituted with one or more hydroxyl groups, and with one or more compounds selected from the following compounds (b), (c) and (d):

(b) a sulfonating agent selected from a vinylsulfonic acid, a C$_{1-5}$ haloalkanesulfonic acid which may be substituted with one or more hydroxyl groups, an epoxy-containing C$_{2-6}$ sulfonic acid, or a salt thereof, (c) a carboxylating agent selected from a halogenated C$_{2-6}$ carboxylic acid which may be substituted with one or more hydroxyl groups, and a salt thereof, and (d) a cationizing agent represented by the following formula (4):

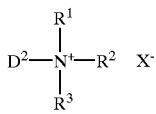

(4)

wherein $D^2$ represents an epoxylated $C_{3-6}$ alkyl group or a halogenated linear or branched $C_{1-6}$ hydrocarbon group which may be substituted with one or more hydroxyl groups, and $R^1$, $R^2$ and $R^3$ may be the same or different and each independently represent a linear of branced $C_{1-3}$ alkyl group which may be substituted with one or more hydroxyl groups, and $X^-$ represents a hydroxy ion, a halogen ion or an organic acid ion.

5. A thickener comprising the polysaccharide derivative according to claim 1.

6. An emulsifier comprising the polysaccharide derivative according to claim 1.

7. An aqueous composition comprising the polysaccharide derivative according to claim 1.

8. The polysaccharide derivative according to claim 1, wherein the degree of substitution is 0.001 to 0.1 per constituent monosaccharide residual group.

9. The polysaccharide derivative according to claim 1, wherein a part or all of the hydrogen atoms of the hydroxyl groups in the polysaccharide derivative are further replaced with substituent group (B)

(B) a $C_{1-5}$ sulfoalkyl group or salt thereof, each of which may be substituted with one or more hydroxyl groups.

10. The polysaccharide derivative according to claim 9, wherein the degree of substitution of the polysaccharide, or the derivative thereof, with the substituent group (B) is 0 to 1.0 per constituent monosaccharide residual group.

11. The polysaccharide derivative according to claim 1, wherein a part or all of the hydrogen atoms of the hydroxyl groups in the polysaccharide derivative are further replaced with substituent group (C)

(C) a $C_{2-6}$ carboxyalkyl group or salt thereof, each of which may be substituted with one or more hydroxyl groups.

12. The polysaccharide derivative according to claim 11, wherein the degree of substitution of the polysaccharide, or the derivative thereof, with the substituent group (C) is 0 to 1.0 per constituent monosaccharide residual group.

13. The polysaccharide derivative according to claim 1, wherein a part or all of the hydrogen atoms of the hydroxyl groups in the polysaccharide derivative are further replaced with substituent group (D)

(D) a group represented by the following formula (2):

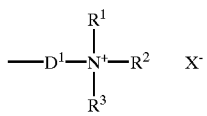

(2)

wherein $D^1$ represents a linear or branched, divalent, saturated $C_{1-6}$ hydrocarbon group which may be substituted with one or more hydroxyl groups $R^1$, $R^2$ and $R^3$ may be the same or different and each independently represent a linear or branched $C_{1-3}$ alkyl group which may be substituted with one or more hydroxyl groups and X— represents hydroxyl ion, a halogen ion or an organic acid ion.

14. The polysaccharide derivative according to claim 13, wherein the degree of substitution of the polysaccharide, or the derivative thereof, with the substituent group (D) is 0 to 0.5 per constituent monosaccharide residual group.

15. The polysaccharide derivative according to claim 2, wherein each of the hydrogen atom(s) of one or more hydroxyl groups in one or more of the substituent groups (A), (B), (C), or (D) is further replaced with one or more substituent groups selected from the group consisting of the substituent group (A), the substituent group (B), the substituent group (C), and the substituent group (D).

16. A thickener comprising the polysaccharide derivative according to claim 2.

17. An emulsifier comprising the polysaccharide derivative according to claim 2.

18. An aqueous composition comprising the polysaccharide derivative according to claim 2.

19. The aqueous composition according to claim 18, wherein the polysaccharide derivative is at a concentration of 0.01 to 5 wt %.

20. The aqueous composition according to claim 18, further comprising one or more hydrophobic compounds selected from the group consisting of a higher alcohol, a sterol, a silicone, a fluorine containing oil, and an oil component.

21. The aqueous composition according to claim 20, wherein said hydrophobic compound is at a concentration of 0.0001 to 50 wt %.

22. The aqueous composition according to claim 7, wherein the polysaccharide derivative is at a concentration of 0.01 to 5 wt %.

23. The aqueous composition according to claim 7, further comprising one or more hydrophobic compounds selected from the group consisting of a higher alcohol, a sterol, a silicone, a fluorine containing oil, and an oil component.

24. The aqueous composition according to claim 23, wherein said hydrophobic compound is at a concentration of 0.0001 to 50 wt %.

25. The polysaccharide derivative according to claim 2, wherein a part or all of the hydrogen atoms of the hydroxyl groups in the polysaccharide derivative are further substituted with substituent group (B)

(B) a $C_{1-5}$ sulfoalkyl group or salt thereof, each of which may be substituted with one or more hydroxyl groups.

26. The polysaccharide derivative according to claim 25, wherein the degree of substitution of the polysaccharide, or the derivative thereof, with the substituent group (B) is 0 to 1.0 per constituent monosaccharide residual group.

27. The polysaccharide derivative according to claim 2, wherein a part or all of the hydrogen atoms of the hydroxyl groups in the polysaccharide derivative are further replaced with substituent group (C)

(C) a $C_{2-6}$ carboxyalkyl group or salt thereof, each of which may be substituted with one or more hydroxyl groups.

28. The polysaccharide derivative according to claim 27, wherein the degree of substitution of the polysaccharide, or the derivative thereof, with the substituent group (C) is 0 to 1.0 per constituent monosaccharide residual group.

29. The polysaccharide derivative according to claim 2, wherein a part or all of the hydrogen atoms of the hydroxyl groups in the polysaccharide derivative are further replaced with substituent group (D)

(D) a group represented by the following formula (2):

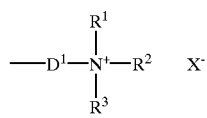

(2)

wherein $D^1$ represents a linear or branched, divalent, saturated $C_{1-6}$ hydrocarbon group which may be substituted with one or more hydroxyl groups $R^1$, $R^2$ and $R^3$ may be the same or different and each independently represent a linear or branched $C_{1-3}$ alkyl group which may be substituted with one or more hydroxyl groups and X— represents hydroxyl ion, a halogen ion or an organic acid ion.

30. The polysaccharide derivative according to claim 29, wherein the degree of substitution of the polysaccharide, or the derivative thereof, with the substituent group (D) is 0 to 0.5 per constituent monosaccharide residual group.

* * * * *

UNITED STATES PATENT AND TRADEMARK OFFICE
CERTIFICATE OF CORRECTION

PATENT NO. : 6,541,614 B1  Page 1 of 1
DATED : April 1, 2003
INVENTOR(S) : Atsushi Nagasawa et al.

It is certified that error appears in the above-identified patent and that said Letters Patent is hereby corrected as shown below:

Column 19,
Line 53, "as" should read -- As --

Column 20,
Line 17, "hydroxyl groups" should read -- hydroxyl groups, --

Column 21,
Line 64, "hydroxyl groups" should read -- hydroxyl groups, --

Column 23,
Line 11, "hydroxyl groups" should read -- hydroxyl groups, --

Column 24,
Line 4, "X—" should read -- $X^-$ --

Signed and Sealed this

Fifteenth Day of July, 2003

JAMES E. ROGAN
*Director of the United States Patent and Trademark Office*